US010456107B2

(12) United States Patent
Schueneman et al.

(10) Patent No.: US 10,456,107 B2
(45) Date of Patent: Oct. 29, 2019

(54) ULTRASOUND IMAGING DEVICE AND METHOD FOR TRANSMITTING AUDIBLE SOUNDS

(71) Applicant: General Electric Company, Schenectady, NY (US)

(72) Inventors: Todd Schueneman, Pewaukee, WI (US); Jonathan Boomgaarden, Waukesha, WI (US); Ross Stalter, Hartland, WI (US); Michael Harland, Shorewood, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/269,103

(22) Filed: Feb. 6, 2019

(65) Prior Publication Data

US 2019/0254625 A1 Aug. 22, 2019

Related U.S. Application Data

(63) Continuation of application No. 15/899,767, filed on Feb. 20, 2018, now abandoned.

(51) Int. Cl.
| | |
|---|---|
| *A61B 8/00* | (2006.01) |
| *H04R 1/02* | (2006.01) |
| *H04R 5/02* | (2006.01) |
| *H04R 3/12* | (2006.01) |
| *G01N 29/06* | (2006.01) |
| *G01S 7/52* | (2006.01) |

(52) U.S. Cl.
CPC .......... *A61B 8/4422* (2013.01); *A61B 8/4427* (2013.01); *A61B 8/461* (2013.01); *H04R 1/028* (2013.01); *H04R 3/12* (2013.01); *H04R 5/02* (2013.01); *G01N 29/0672* (2013.01); *G01S 7/52085* (2013.01); *H04R 2400/11* (2013.01)

(58) Field of Classification Search
CPC ..... A61B 8/4422; A61B 8/4427; A61B 8/461; H04R 1/028; H04R 3/12; H04R 5/02; H04R 2400/11; G01N 29/0272; G01N 7/52085
See application file for complete search history.

(56) References Cited

U.S. PATENT DOCUMENTS

| | | | | |
|---|---|---|---|---|
| 2015/0298174 | A1* | 10/2015 | Bibl | B06B 1/0644 310/316.01 |
| 2016/0381480 | A1* | 12/2016 | Takenouchi | H04R 29/004 381/58 |
| 2019/0059851 | A1* | 2/2019 | Rothberg | A61B 8/0883 |
| 2019/0122018 | A1* | 4/2019 | Kho | G06K 9/0002 |

* cited by examiner

*Primary Examiner* — Andrew L Sniezek (57) ABSTRACT

An ultrasound imaging device includes an exterior housing including a panel, a processor positioned within the exterior housing, and an acoustic exciter attached to the panel and electrically connected to the processor. The processor is configured to drive the acoustic exciter in order to vibrate the panel and transmit audible sounds. A method of providing audible sounds from an ultrasound device includes attaching an acoustic exciter to a panel, electrically connecting the acoustic exciter to a processor, providing signals to the acoustic exciter from the processor, vibrating the acoustic exciter in response to the signals, and transmitting audible sounds from the panel connected to the acoustic exciter.

20 Claims, 9 Drawing Sheets

FIG. 10

ULTRASOUND IMAGING DEVICE AND METHOD FOR TRANSMITTING AUDIBLE SOUNDS

CROSS-REFERENCE TO RELATED APPLICATIONS

The present application is a continuation of U.S. patent application Ser. No. 15/899,767, filed on Feb. 20, 2018, which is incorporated herein by reference in its entirety.

FIELD OF THE INVENTION

This disclosure relates generally to an ultrasound imaging device including an acoustic emitter and a method for transmitting audible sounds from the ultrasound imaging device.

BACKGROUND OF THE INVENTION

Ultrasound imaging is a radiation-free imaging modality that is used in a wide variety of different care areas. Due to its non-ionizing nature, the portability of the systems, and the relatively low cost compared to other imaging modalities, ultrasound is relied upon to diagnose and monitor a wide variety of different health conditions. For example, ultrasound imaging is routinely used within areas including: cardiac, obstetrics, angiography, musculoskeletal, general imaging, as well as many other areas.

Due to the widespread adoption of ultrasound imaging devices for many clinical uses, ultrasound imaging devices tend to see relatively heavy-use in a large number of different clinical settings. In order to ensure patient safety, it is important to ensure that the ultrasound imaging devices are regularly cleaned/sterilized in order to minimize the risk of transmitting infectious diseases and/or bacteria.

Ultrasound imaging devices are typically cleaned at least daily. And, in some clinical use areas, ultrasound imaging devices may need to cleaned/sterilized between each patient. Cleaning the ultrasound imaging device is an onerous task that must be performed thoroughly in order to minimize patient risk. The task of cleaning and/or sterilizing an ultrasound imaging device is made more difficult by the presence of cracks or seams in the exterior surface of the ultrasound imaging device. Conventional ultrasound imaging devices typically include one or more speakers for transmitting audible sounds to a user. Each conventional speaker includes a magnet attached to a flexible cone that moves in response to electrical signals. The movement of the cone generates pressure waves that are perceived by the user as sound. However, in order to effectively transmit sound waves, it is necessary to mount the speakers behind a portion of a panel with multiple speaker holes or openings that are directed at the user. Mounting the conventional speaker behind a solid panel would muffle the sound by effectively blocking the sound waves from reaching the user. Thus, conventional speakers typically require a number of small speaker holes or openings within panels used to form the housing of the ultrasound imaging device. In order to effectively transmit audible sounds, it is typically necessary to position the speaker holes or opening in locations that make them very susceptible to contamination from blood and/or other body fluids when used in a medical environment. The speaker openings and the areas around the speaker openings are difficult and time-consuming to adequately clean and disinfect.

For these and other reasons an improved ultrasound imaging device and method for transmitting audible sounds without requiring speaker holes or openings is desired.

BRIEF DESCRIPTION OF THE INVENTION

The above-mentioned shortcomings, disadvantages and problems are addressed herein which will be understood by reading and understanding the following specification.

In an embodiment, an ultrasound imaging device includes an exterior housing including a panel, a processor positioned within the exterior housing, and an acoustic exciter attached to the panel and electrically connected to the processor. The processor is configured to drive the acoustic exciter in order to vibrate the panel and transmit audible sounds, using the panel as a sound-excited assembly.

In an embodiment, a method of providing audible sounds from an ultrasound device includes attaching an acoustic exciter to a panel, electrically connecting the acoustic exciter to a processor, assembling the panel to at least one of a frame and a second panel to construct an exterior housing, wherein the exterior housing encloses the processor and the acoustic exciter, providing signals to the exciter from the processor, vibrating the acoustic exciter in response to the signals, and transmitting the audible sounds from the panel connected to the vibrating acoustic exciter.

In an embodiment, an ultrasound imaging device includes an exterior housing including a panel, where the panel comprises an interior surface and an exterior surface, where the exterior surface defines a surface without speaker openings to aid in cleaning the panel. The ultrasound imaging device includes an acoustic exciter rigidly attached to the interior surface of the panel, and a processor disposed within the exterior housing and electrically connected to the acoustic exciter. The combination of the acoustic exciter and the panel functions as a sound-excited assembly to transmit audible sounds in response signals provided by the processor.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
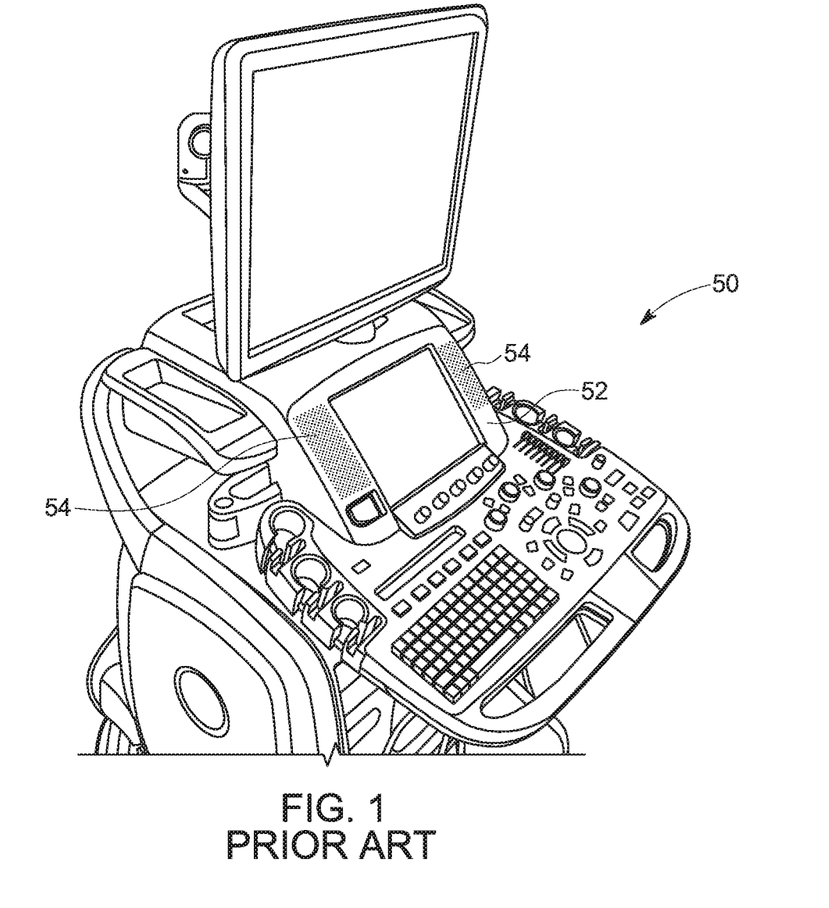
FIG. 1 is a perspective view of a prior art ultrasound imaging device.

FIG. 1 is a perspective view of a prior art ultrasound imaging device 50. Ultrasound imaging device 50 includes a panel 52 with a plurality of speaker holes 54. The panel 52 is shaped to define the plurality of speaker holes 54 to allow acoustic signals generated from a speaker mounted behind the panel 52 to reach the operator scanning with the ultrasound imaging device 50. As discussed hereinabove, the plurality of speaker holes 54 provides cavities for dirt and bacteria to accumulate. Therefore, the speaker holes 54 make it much more difficult for the operator to clean and/or sterilize the ultrasound imaging device 50.

Figure 2:
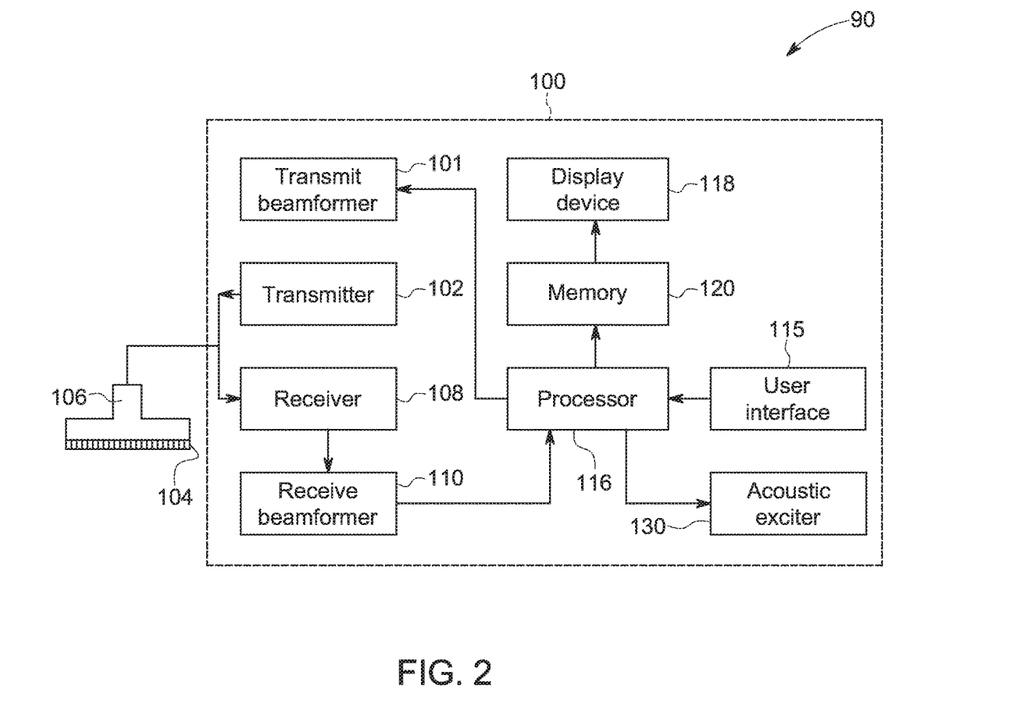
FIG. 2 is a schematic diagram of an ultrasound imaging system in accordance with an embodiment.

FIG. 2 is a schematic diagram of an ultrasound imaging system 90 in accordance with an embodiment. The ultrasound imaging system 90 includes an ultrasound imaging device 100 and a probe 106. The ultrasound imaging device 100 includes a transmit beamformer 101 and a transmitter 102 that drive elements 104 within a probe 106 to emit pulsed ultrasonic signals into a body (not shown). The probe 106 may be an 2D array probe according to an embodiment. However, any other type of probe that is fully steerable in an elevation direction and capable of acquiring four-dimensional (4D) ultrasound data may be used according to other embodiments. For purposes of this disclosure, the term four-dimensional ultrasound data, or 4D ultrasound data, is defined to include ultrasound data including multiple volumes of a region-of-interest acquired over a period of time. The 4D ultrasound data contains information about how a volume changes over time. Each of the volumes may include a plurality of 2D images or slices. The pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user interface 115 may be used to control operation of the ultrasound imaging system 90, including, to control the input of patient data, to change a scanning or display parameter, and the like.

The ultrasound imaging device 100 also includes a processor 116 to control the transmit beamformer 101, the transmitter 102, the receiver 108 and the receive beamformer 110. The processor 116 is in electronic communication with the probe 106. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire and display data a real-time volume-rate of 7-20 volumes/sec. However, it should be understood that the real-time frame rate may be dependent on the length of time that it takes to acquire each volume of data. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging device 100 may continuously acquire data at a volume-rate of, for example, 10 Hz to 30 Hz. Images generated from the data may be refreshed at a similar volume-rate. Other embodiments may acquire and display data at different rates. For example, some embodiments may acquire data at a volume-rate of less than 10 Hz or greater than 30 Hz depending on the size of the volume and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

The ultrasound imaging device 100 also includes an acoustic emitter 130 in electronic communication with the processor 116. Ultrasound imaging devices may include more than one acoustic emitters 130 according to various embodiments. The acoustic emitter 130 is configured to vibrate in response to signals received from the processor 116. The signals transmitted from the processor 116 may, for instance, be the same type of signals that would be transmitted to a speaker in a conventional system. The acoustic emitter 130 contains a magnet and the acoustic emitter 130 is designed to impart vibrations to a panel of the ultrasound imaging device. Instead of moving a cone, as in a traditional speaker, the acoustic emitter 130 vibrates the panel to which it is attached, and the vibrations of the panel create sound waves. Additional details about the acoustic emitter 130 will be provided hereinafter with respect to different figures.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 3:
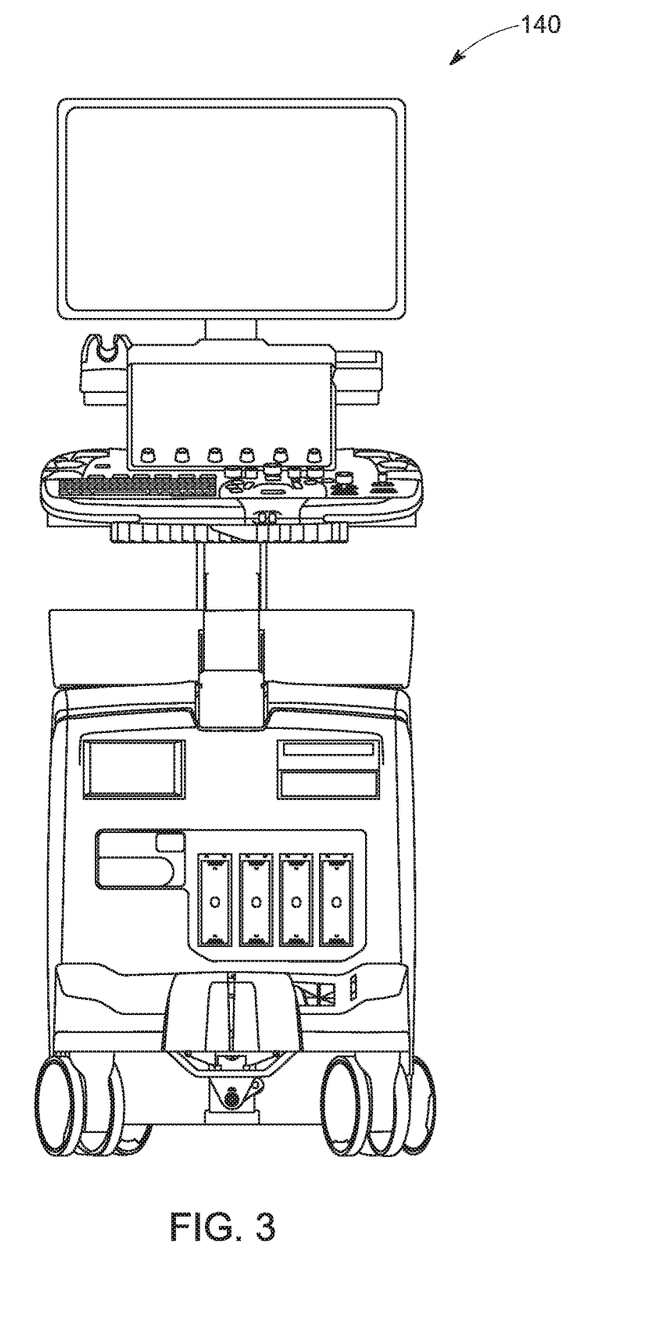
FIG. 3 is a front view an ultrasound imaging device in accordance with an embodiment.

FIG. 3 is a front view the ultrasound imaging device 140 in accordance with an embodiment. The ultrasound imaging device 140 shown in FIG. 3 is an ultrasound imaging console. The ultrasound imaging device 140 may include all of the components represented in the schematic view of the ultrasound imaging device 100 (shown in FIG. 2) in accordance with an example. However, it should be appreciated that, according to other embodiments, the ultrasound imaging device may be a different size and/or shape. For example, according to other embodiments, the ultrasound imaging device may be a laptop-style ultrasound imaging device, such as the ultrasound imaging device 145, shown in FIG. 4, or a hand-held ultrasound imaging device, such as the ultrasound imaging device 150, shown in FIG. 5. The ultrasound imaging device 145 (shown in FIG. 4) and the ultrasound imaging device 150 shown in FIG. 5, both include all of components represented in the schematic view of the ultrasound imaging device 100 (shown in FIG. 2) in accordance with exemplary embodiments. A front cover 147 is visible in the embodiment shown in FIG. 4. The front cover 147 is one example of a panel that is a component of an external housing for the ultrasound imaging device 145. And a front cover 151 is visible in the embodiment shown in FIG. 5. The front cover 151 is an example of a panel that is a component of an external housing for the ultrasound imaging device 150.

Figure 6:
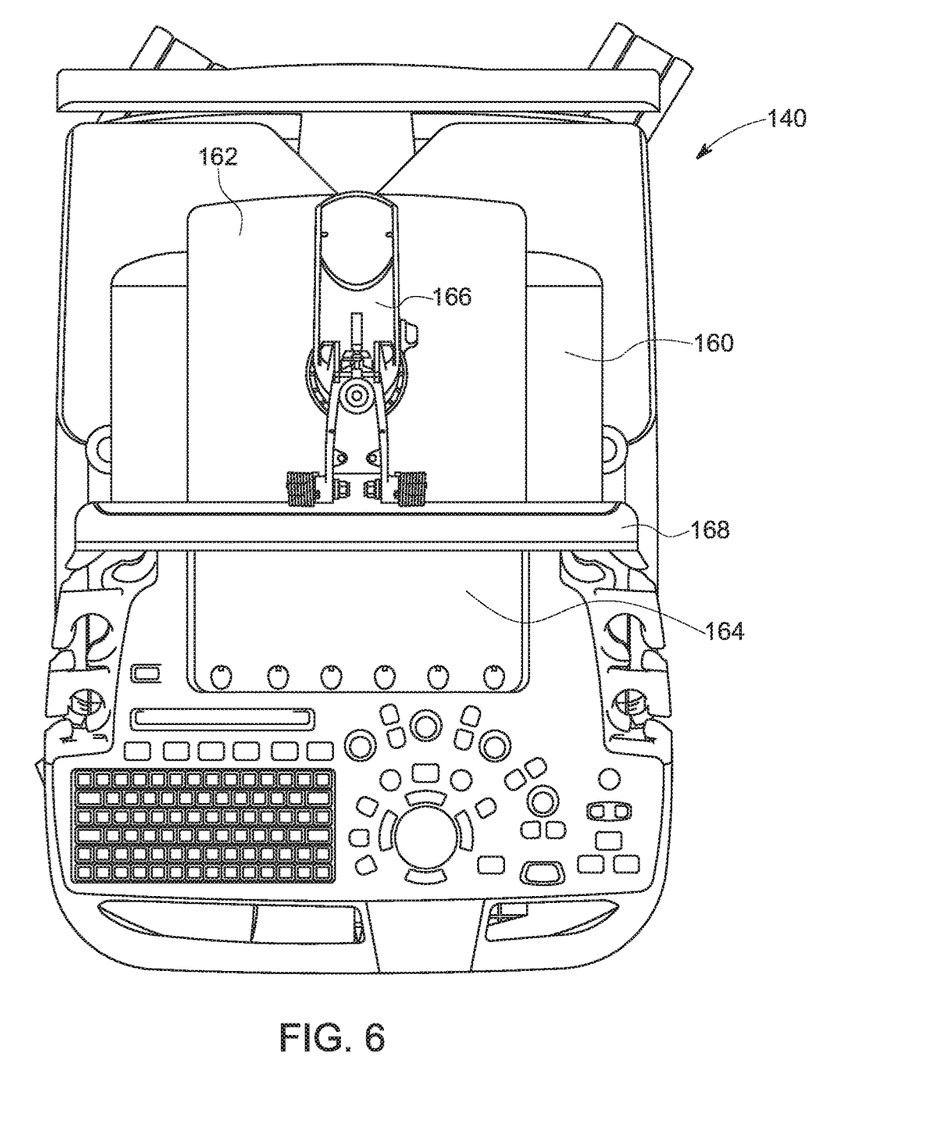
FIG. 6 is a top view of an ultrasound imaging device in accordance with an embodiment.
Figure 7:
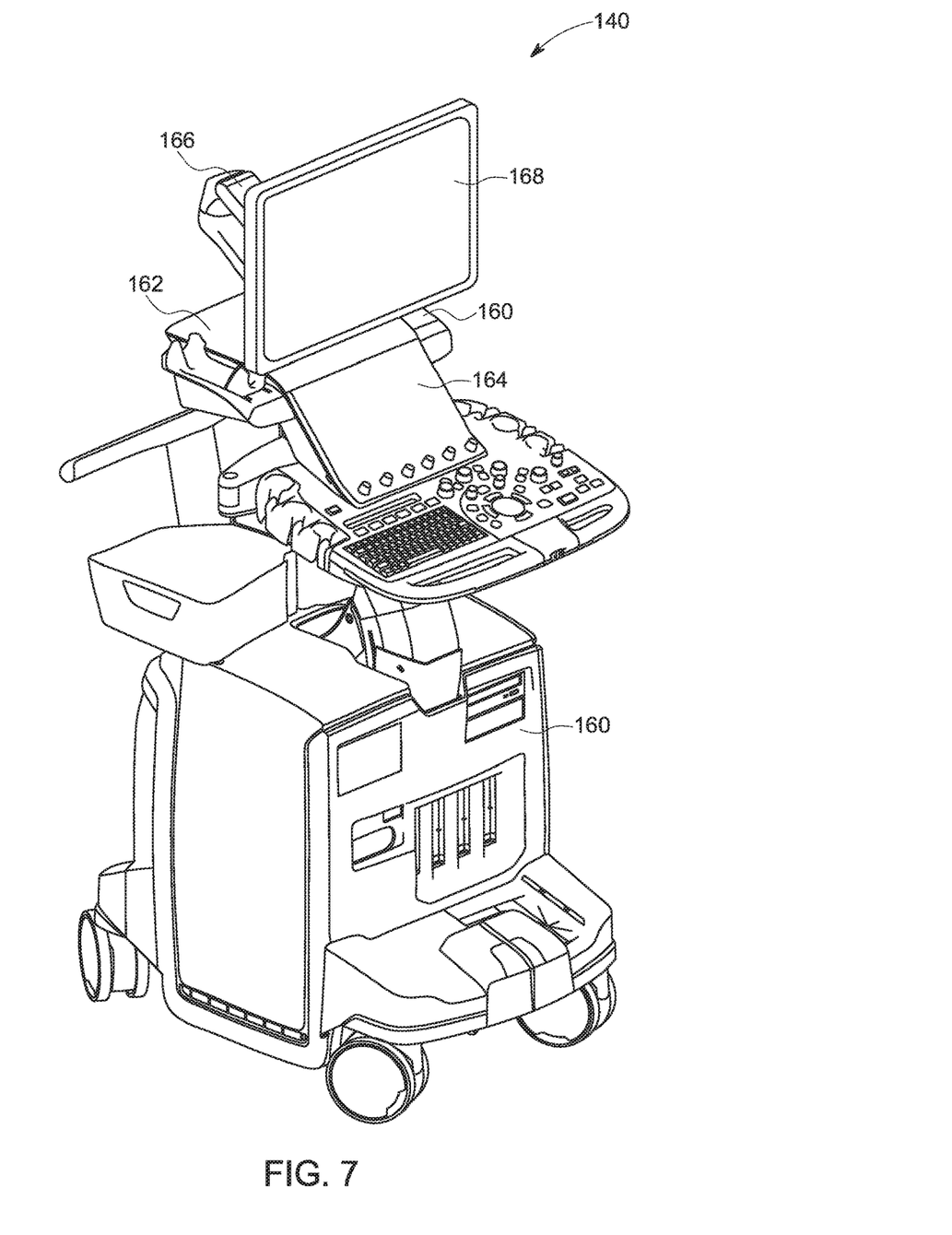
FIG. 7 is a perspective view of an ultrasound imaging device in accordance with an embodiment.

FIG. 6 is a top-view of the ultrasound imaging device 140. FIG. 7 is a perspective view of the ultrasound imaging device 140. Common reference numbers will be used to identify identical components in the figures.

The ultrasound imaging device 140 includes an exterior housing 160. The exterior housing 160 includes a plurality of panels. The exterior housing 160 encloses and protects the processor 116, the memory 120, the acoustic exciter 130, the transmit beamformer 101, the transmitter 102, the receive 108, and the receive beamformer 110. The panels may be made of a variety of materials including various plastics and metal alloys. According to the embodiment shown in FIGS. 3, 6 and 7, the exterior housing includes a top cover 162 and a front cover 164. According to an embodiment, a support arm 166 attaches a display device 168 to the housing through a hole 170 (shown in FIGS. 9 and 10) defined in the top cover 162.

Figure 9:
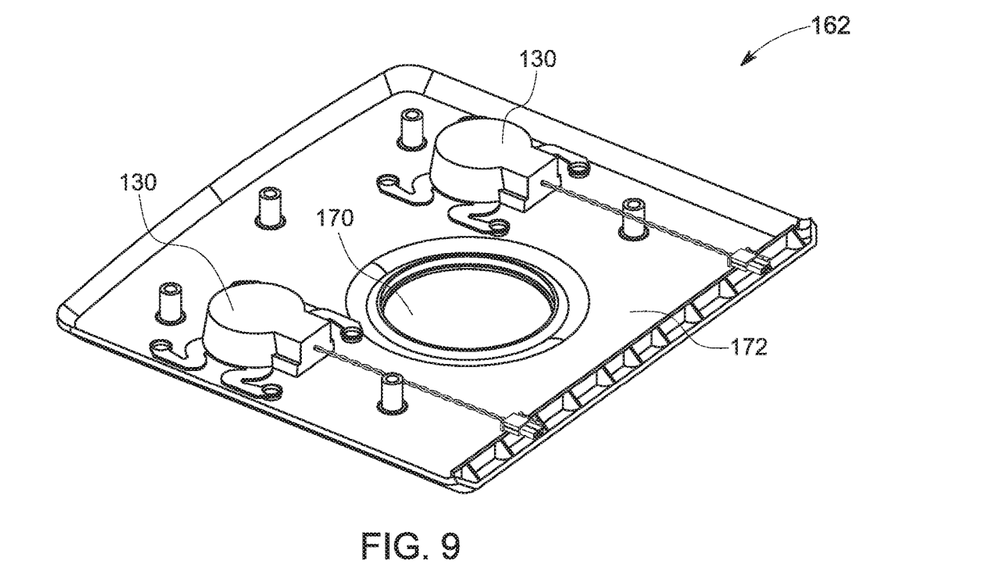
FIG. 9 is a perspective view of a panel in accordance with an embodiment.
Figure 10:
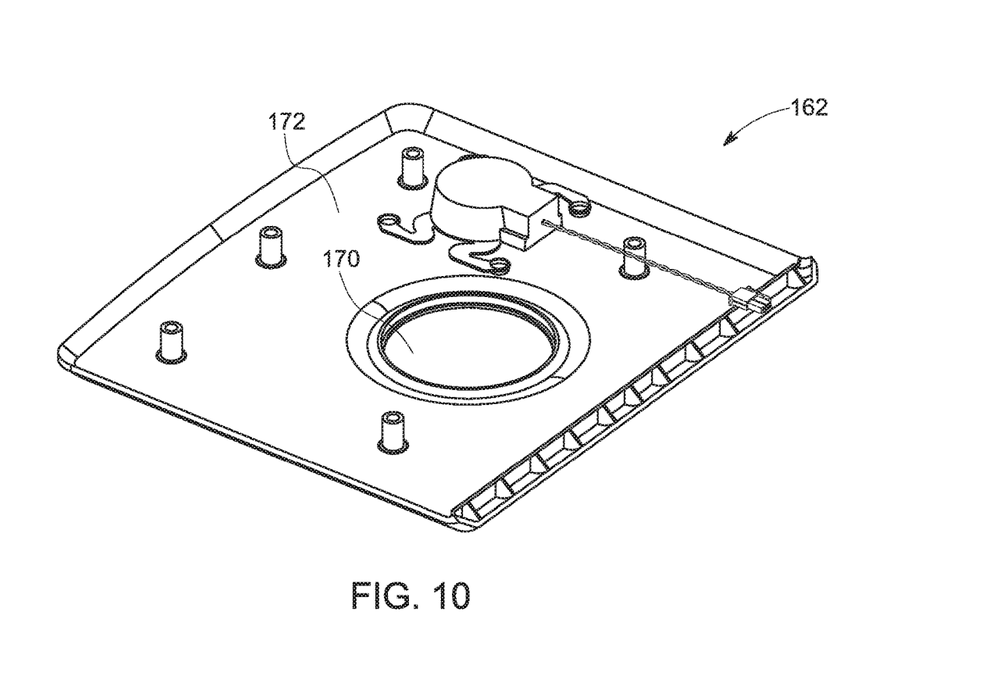
FIG. 10 is a perspective view of a panel in accordance with an embodiment.

FIG. 9 is a perspective view of the top cover 162 in accordance with an embodiment and FIG. 10 is a perspective view of the top cover 162 in accordance with another embodiment.

The exterior housing 160 of the embodiment shown in FIGS. 3, 6, and 7 defines multiple separate areas of enclosure. According to other embodiments, the exterior housing may define only a single area of enclosure, such as in the hand-held ultrasound imaging device 150 shown in FIG. 5, or the exterior housing may define more than two areas of enclosure (not shown).

Figure 8:
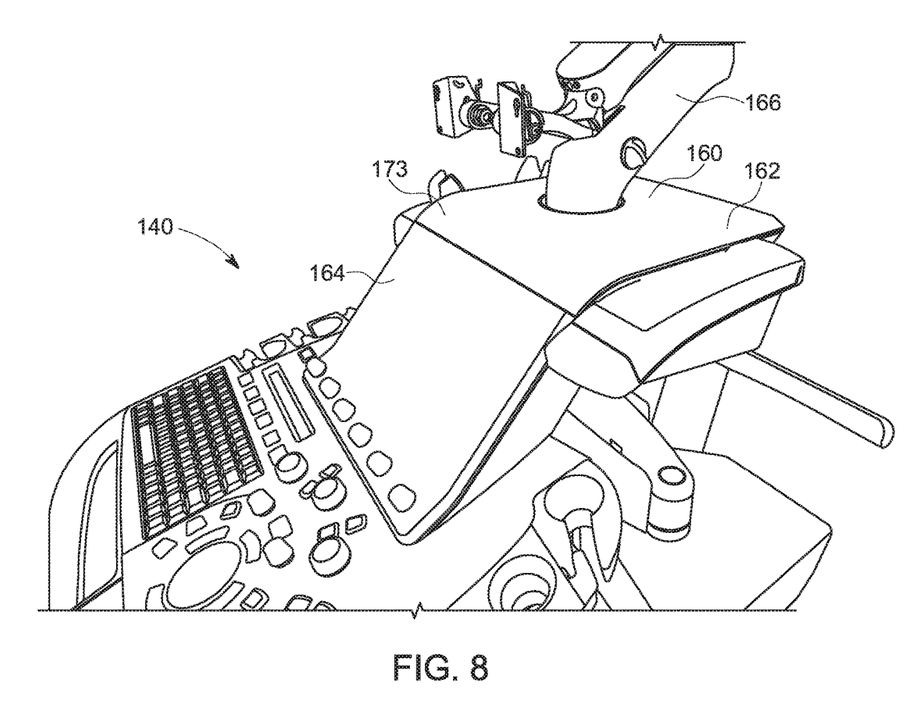
FIG. 8 is a perspective view of a portion of an ultrasound imaging device in accordance with an embodiment.

Each of the panels in the housing 160, such as the top cover 162 or the front cover 164 includes an interior surface and an exterior surface. For example, an interior surface 172 of the top cover 162 is visible in FIGS. 9 and 10. An exterior surface 173 of the top cover 162 is visible in FIG. 8. The interior surface 172 faces the inside of the area of enclosure defined by the housing, while the exterior surface 173 is visible on the exterior of the ultrasound imaging device 140.

According to the embodiment shown in FIG. 9, a pair of acoustic emitters 130 are attached to the interior surface of the top cover 162. As described hereinabove, each of the acoustic emitters 130 may include a magnet that causes each acoustic emitter 130 to vibrate in response to receiving signals from the processor 116. Each acoustic emitter 130 may be rigidly mounted to the top cover 162. For example, each acoustic emitter 130 may be affixed with tape or an adhesive, such as epoxy. Each acoustic emitter 130 may be attached to the top cover 162 by other mechanical techniques according to other embodiments.

A first one of the acoustic emitters 130 attached to the top cover 162 may receive a first signal along a first channel and a second of the acoustic emitters 130 may receive a second signal along a second channel. The processor 116 may provide identical signals to both of the acoustic emitters 130, or the processor 116 may transmit slightly different signals to each of the acoustic emitters 130 in order to emit audible sounds in stereo. According to another embodiment, a first emitter 130 may be attached to a first panel and a second emitter 130 may be attached to a second panel which is physically separated from the first panel. Increasing the separation between the two panels emitting different audible sounds may be used to increase the stereo separation between signals coming from two or more different channels.

Since acoustic emitter 130 is rigidly mounted to the top cover 162, vibrations from each acoustic emitter 130 are transmitted to the top cover 162. The top cover 162, in turn, generates sound waves while it is vibrating. By using the processor 116 to modulate the frequency at which each acoustic emitter 130 vibrates, the processor 116 controls the sounds transmitted from the top cover. The combination of one or more acoustic emitters 130 attached to a panel function as a sound-excited assembly. The sound-excited assembly, acts like a speaker. Each acoustic emitter 130 vibrates at a frequency that is modulated by the processor 116, and the attached panel also vibrates at the same, or a very similar frequency. The vibration of the panel generates sound waves which are detectable by an operator.

The sound-excited assembly may be used to communicate/transmit any type of audible noises to the user. For example, the sound-excited assembly may be used to communicate audible instructions to a user, various warning chimes or notes, or information indicative of flow information in the ultrasound data, such as when acquiring Doppler or Color ultrasound data.

The size and/or number of acoustic emitters attached to a specific panel depends on a variety of factors. Specifically, the size of the panel and the stiffness of the panel. The stiffness of the panel depends upon the material used for the panel, the thickness of the panel and the three-dimensional shape of the panel. Larger and/or stiffer panels necessitate more powerful acoustic emitters or a larger number of smaller acoustic emitters. FIG. 10, for example, shows an exemplary embodiment of the top cover 162 with only a single acoustic emitter 130 attached to the top cover 162. A single acoustic emitter 130 may be used for ultrasound imaging devices with only a single channel carrying signals used to generate audible signals.

According to another embodiment, one or more acoustic emitters 130 may be attached to an interior surface of a front cover, such as the front cover 164. While the front cover 164 and the top cover 162 were both explicitly given as examples of panels to which acoustic emitters may be attached, it should be appreciated by those skilled in the art that one or more acoustic emitters 130 may be attached to any panel of the exterior housing 160 in other embodiments. Any selected panel with an acoustic emitter 130 attached to it may function as a sound-excited assembly in a manner similar to that which was described with respect to the top cover 162.

Figure 4:
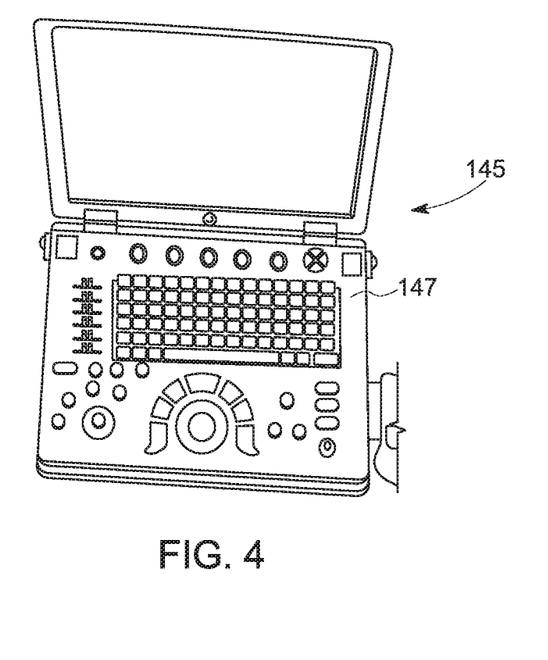
FIG. 4 is an ultrasound imaging device in accordance with an embodiment.
Figure 5:
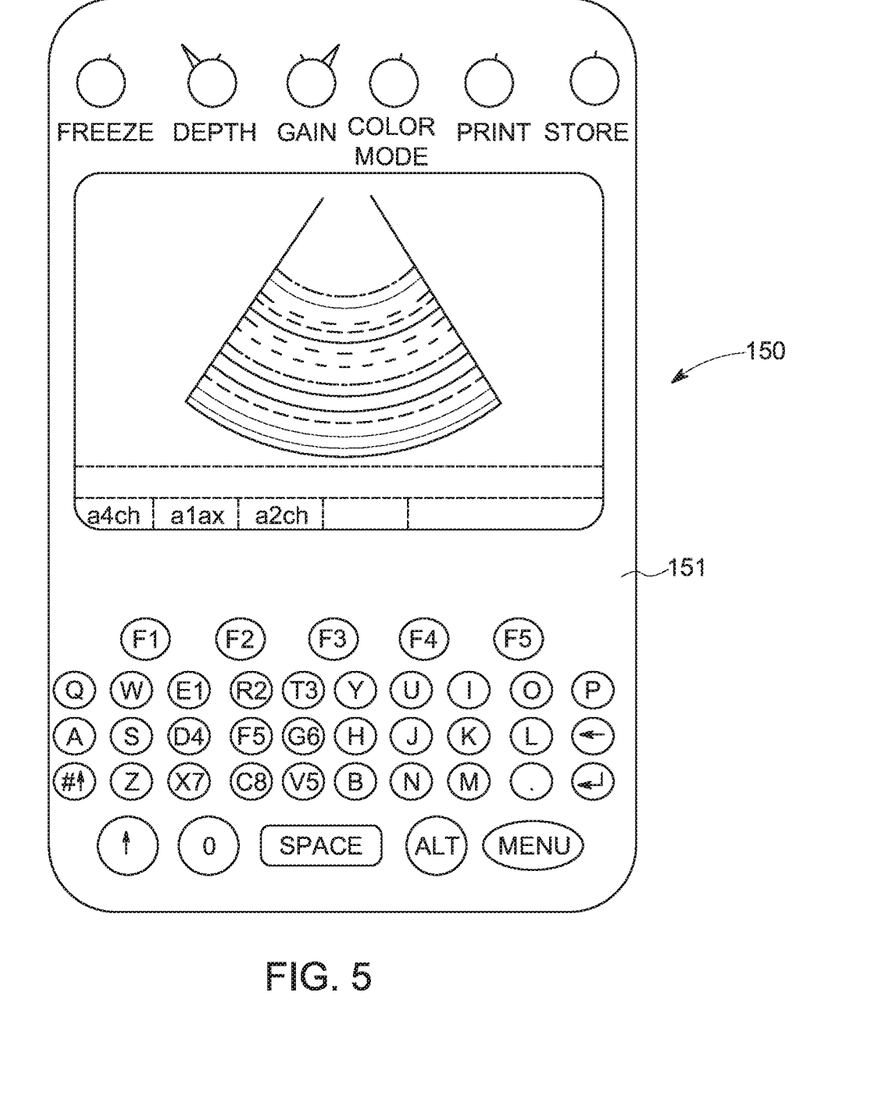
FIG. 5 is an ultrasound imaging device in accordance with an embodiment

Likewise, one or more panels from either a laptop-style ultrasound device, such as the ultrasound imaging device 145 shown in FIG. 4 or a handheld ultrasound device, such as the ultrasound imaging device 150 shown in FIG. 5 may function as a sound-excited assembly through the attachment of one or more acoustic exciters 130.

There are numerous advantages to using an acoustic exciter attached to a panel as a sound-excited assembly as described hereinabove. First, and most significantly, it is possible to use a panel with an exterior surface that is a seamless surface, such as the top cover 162. The top cover 162 does not have any seams or and it does not define any speaker openings. The top cover 162, and as a result, the ultrasound imaging device 140, are therefore much easier to clean and or sterilize than a convention ultrasound imaging device including a convention speaker with speaker openings. By not having speaker openings, the ultrasound imaging device naturally stays cleaner (i.e., there are less spaces and gaps for dirt or bacteria to accumulate), and it is easier to clean because the top cover, or any other panel used as a sound-excited assembly, may have a seamless exterior surface.

Second, conventional speakers are directional. That is, they transmit sound more effectively in one direction compared to other directions. As such, it is necessary to orient the speakers, and any accompanying speaker openings, towards the user for the user to hear clear audible sounds generated from the speaker. In contrast, using a panel with an attached acoustic exciter as a sound-excited assembly results in an omnidirectional source of sound. That is, the sound may be heard clearly in all directions. This affords the ultrasound manufacturer much more freedom regarding the placement of the sound-excited assembly. This can free-up room on the front side of the ultrasound imaging system for additional user interface controls, a larger screen, or it may allow for reducing the overall form factor of the ultrasound imaging device.

Third, by mounting the acoustic exciters to the interior surface of a panel, the acoustic exciters are protected from the environment. Ultrasound imaging devices are frequently subjected to harsh cleaning agents that can be damaging to electronics. By placing the acoustic exciters on the interior surface, the acoustic exciters, and associated channel wiring, are much more isolated from environmental conditions compared to a conventional speaker with speaker openings in the panel.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An ultrasound imaging system comprising:
   a probe comprising a plurality of elements; and
   an ultrasound imaging device comprising:
   an exterior housing comprising a panel;
   a processor positioned within the exterior housing; and
   an acoustic emitter attached to the panel and electrically connected to the processor;
   wherein the processor is configured to control the acoustic emitter to vibrate the panel and transmit audible sounds, using the panel as a sound-excited assembly; and
   wherein the processor is configured to control the plurality of elements in the probe to emit ultrasonic signals.

2. The ultrasound imaging system of claim 1, wherein the ultrasound imaging device is a laptop-style ultrasound imaging device.

3. The ultrasound imaging system of claim 2, wherein the panel is one of a front cover and a top cover.

4. The ultrasound imaging system of claim 1, wherein the ultrasound imaging device is a hand-held ultrasound imaging device.

5. The ultrasound imaging system of claim 4, wherein the panel is a front cover.

6. The ultrasound imaging system of claim 1, wherein the acoustic emitter comprises a magnet that causes the acoustic emitter to vibrate in response to receiving signals from the processor.

7. The ultrasound imaging system of claim 1, wherein the acoustic emitter is mounted to an interior surface of the panel opposite a seamless exterior surface of the panel.

8. The ultrasound imaging system of claim 7, wherein the acoustic emitter is mounted to the interior surface of the panel using at least one of a piece of tape, an adhesive, and a mechanical structure.

9. The ultrasound imaging system of claim 1, wherein the ultrasound imaging device is an ultrasound imaging console.

10. The ultrasound imaging system of claim 9, wherein the panel is one of a front cover and a top cover.

11. The ultrasound imaging system of claim 1, wherein the panel is a top cover, and wherein the ultrasound imaging system includes a support arm attached to a display device, and wherein the top cover defines a hole, and wherein the support arm passes through the hole defined in the top cover.

12. The ultrasound imaging system of claim 11, further comprising a second acoustic emitter attached to the panel and electrically connected to the processor.

13. The ultrasound imaging system of claim 12, wherein the hole defined by the housing is positioned in between the first acoustic exciter and the second acoustic exciter.

14. The ultrasound imaging system of claim 1, further comprising a second acoustic emitter attached to the panel and electrically connected to the processor.

15. The ultrasound imaging system of claim 14, wherein the processor is configured to provide identical signals to both the acoustic emitter and the second acoustic emitter.

16. The ultrasound imaging system of claim 14, wherein the processor is configured to provide first signals to the acoustic emitter and second signals to the second acoustic emitter, where the first signals are different from the second signals in order to transmit the audible sounds from the panel in stereo.

17. The ultrasound imaging system of claim 16, wherein the processor is configured to provide first signals to the acoustic emitter and second signals to the second acoustic emitter, where the first signals are different from the second signals to transmit the audible sounds from the panel in stereo.

18. The ultrasound imaging system of claim 14, wherein the processor is configured to provide identical signals to both the acoustic emitter and the second acoustic emitter.

19. The ultrasound imaging system of claim 1, wherein the exterior housing comprises a second panel, wherein the ultrasound imaging system further comprises a second acoustic emitter attached to the second panel.

20. The ultrasound imaging system of claim 1, wherein the exterior housing defines a surface without speaker openings to aid in cleaning the exterior housing.

* * * * *